(12) United States Patent
Jou et al.

(10) Patent No.: US 9,266,833 B2
(45) Date of Patent: Feb. 23, 2016

(54) CARRIER TRANSPORT MATERIAL

(71) Applicant: National Tsing Hua University, Hsinchu (TW)

(72) Inventors: Jwo-Huei Jou, Hsinchu (TW); Tsung-Han Li, Tainan (TW); Saulius Grigalevičius, Kaunas (LT); Gintarė Kručaitė, Kupiskio District (LT)

(73) Assignee: National Tsing Hua University (TW)

( * ) Notice: Subject to any disclaimer, the term of this patent is extended or adjusted under 35 U.S.C. 154(b) by 0 days.

(21) Appl. No.: 14/340,560

(22) Filed: Jul. 25, 2014

(65) Prior Publication Data

US 2016/0028013 A1  Jan. 28, 2016

(51) Int. Cl.
  *C07D 209/86* (2006.01)
  *C07D 209/88* (2006.01)
  *C07D 403/14* (2006.01)
  *H01L 51/00* (2006.01)
  *H01L 51/50* (2006.01)

(52) U.S. Cl.
  CPC ............ *C07D 209/86* (2013.01); *C07D 209/88* (2013.01); *C07D 403/14* (2013.01); *H01L 51/005* (2013.01); *H01L 51/0052* (2013.01); *H01L 51/0072* (2013.01); *H01L 51/5056* (2013.01)

(58) Field of Classification Search
  CPC ... C07D 209/86; C07D 209/88; C07D 403/14
  See application file for complete search history.

(56) References Cited

U.S. PATENT DOCUMENTS

2003/0091859 A1 * 5/2003 Cho .................. C07C 22/04
                                                                    428/690

OTHER PUBLICATIONS

Bozano et al. Adv. Funct. Mater. 2005, 15, 1933-1939.*
Rasymaite et al. Optical Materials 2013, 35, 2072-2076.*
C. W. Tang et al. "Organic electroluminescent diodes", Appl. Phys. Lett. 51 (12), 1987.

* cited by examiner

*Primary Examiner* — Matthew Coughlin

(57) ABSTRACT

The present invention provides a carrier transport material formed by completing a reaction process of at least one aromatic compound and at least one polycyclic aromatic hydrocarbons (PAHs), wherein a cross linking reaction can be activated in the molecular compound through heating or ultraviolet irradiation because the molecular compound has at least one cross-linkable functional group. Therefore, when the carrier transport material is applied in an OLED, the carrier transport material would not be dissolved by the solvent included in the next coated material because the carrier transport material has been cured after the cross linking reaction is carried out. Moreover, because the carrier transport material would simultaneously perform an electron confining functionality when being used as a hole transport layer, the device efficiency of the OLED having the carrier transport material is obviously enhanced during the high-brightness operation especially.

2 Claims, 13 Drawing Sheets

CARRIER TRANSPORT MATERIAL

BACKGROUND OF THE INVENTION

1. Field of the Invention

The present invention relates to the technology field of carrier transport materials, and more particularly to a specific carrier transport material capable of being used as a hole transport layer and/or an electron confining layer of an organic light emitting device.

2. Description of the Prior Art

An organic light emitting diode (OLED) was invented by C. W. Tang and S. A. VanSlyk et al. of Eastman Kodak Company in 1987 and manufactured by a vacuum evaporation method. A hole transport material and an electron transport material (such as Alq3) are respectively deposited on a transparent indium tin oxide (abbreviated as ITO) glass, and then a metal electrode is vapor-deposited thereon to form the self-luminescent OLED apparatus. Due to high brightness, fast response speed, light weight, compactness, true color, no difference in viewing angles, no need of liquid crystal display (LCD) type backlight plates as well as a saving in light sources and low power consumption, it has become a new generation display.

Recently, some interlayers such as electron transport layer and hole transport layer are added into the OLEDs for increasing the current efficiency or power efficiency of the OLEDs. For example, the organic light emitting diode (OLED) 1' structure shown as FIG. 1 consists of: a cathode 11', an electron injection layer 13', a light emitting layer 14', a hole transport layer 16', and an anode 18'.

The OLED 1' shown by FIG. 1 can by fabricated by using a solution process. With reference to FIG. 2, there is shown a flow chart of the solution process for manufacturing the OLED; moreover, please simultaneously refer to FIG. 3, which shows the manufacturing process diagrams of the OLED. As shown in FIG. 2 and FIG. 3, the solution process for manufacturing OLED mainly consists of following steps:

First of all, the process flow proceeds to steps (S01') and (S02') for providing a substrate 2' and at least one template 3', wherein the template 3' is formed with a transfer printing pattern 31'. Next, in step (S03'), a plurality of organic light-emitting materials 4' are coated onto the transfer printing pattern 31' through an inking process. Subsequently, the process flow proceeds to steps (S04') for making the organic light-emitting materials 4' coated on the transfer printing pattern 31' be transferred onto the surface of the substrate 2' by a contact printing process. Eventually, at least one light emitting layer 41' is formed on the surface of the substrate 2' in step (S05'). Thus, the OLED 1' shown by FIG. 1 can be mass produced rapidly.

In spite of the solution process can be used for mass produced OLED, the solution process still reveals some shortcoming and drawbacks during practical operations. With reference to FIG. 1, FIG. 2 and FIG. 3, because the manufacturing material of the hole transport layer 13' and the light emitting layer 14' is commonly TAPC ((1,1-Bis[4-[N, N'-di(p-tolyl)amino]phenyl]cyclohexane)) and Spiro-2CBP (2,7-Bis(9-carbazolyl)-9,9-sspirobifluorene) respectively, the Spiro-2CBP would dissolve a portion of TAPC when the Spiro-2CBP is coated onto the hole transport layer 13'. Moreover, the same dissolve situation would also occur between any other two layers during the operation of the solution process. Therefore, it can easily know that the solution process cannot used to fabricate a high-quality OLED because of the limitation of manufacturing materials.

Accordingly, in view of the conventional solution process still including drawbacks, the inventor of the present application has made great efforts to make inventive research thereon and eventually provided a carrier transport material for being a hole transport layer and/or an electron confining layer of the organic light emitting device.

SUMMARY OF THE INVENTION

The primary objective of the present invention is to provide a carrier transport material, which is formed by completing a reaction process of at least one aromatic compound and at least one polycyclic aromatic hydrocarbons (PAHs), wherein a cross linking reaction can be activated in the molecular compound through heating or ultraviolet irradiation because the molecular compound has at least one cross-linkable functional group. Therefore, when the carrier transport material is applied in an OLED, the carrier transport material would not be dissolved by the solvent included in the next coated material because the carrier transport material has been cured after the cross linking reaction is carried out. Moreover, because the carrier transport material would simultaneously perform an electron confining functionality when being used as a hole transport layer, the device efficiency of the OLED having the carrier transport material is obviously enhanced during the high-brightness operation especially.

Accordingly, in order to achieve the primary objective of the present invention, the inventor of the present invention provides a carrier transport material, wherein the carrier transport material is a molecular compound formed by completing a reaction process of at least one aromatic compound and at least one polycyclic aromatic hydrocarbons (PAHs); moreover, the molecular compound having at least one cross-linkable functional group, such that a cross linking reaction can be activated in the molecular compound through heating or ultraviolet irradiation.

According to one embodiment of the carrier transport material, wherein the aromatic compound is represented by following chemical formula 1, chemical formula 2 or chemical formula 3:

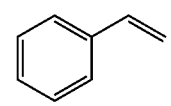

[chemical formula 1]

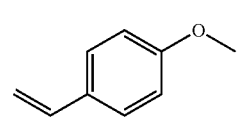

[chemical formula 2]

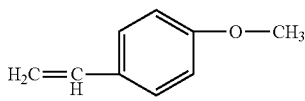

[chemical formula 3]

According to one embodiment of the carrier transport material, wherein the chemical structure of the polycyclic aromatic hydrocarbons (PAHs) is represented by following chemical formula 4, chemical formula 5, chemical formula 6, chemical formula 7, chemical formula 8, or chemical formula 9:

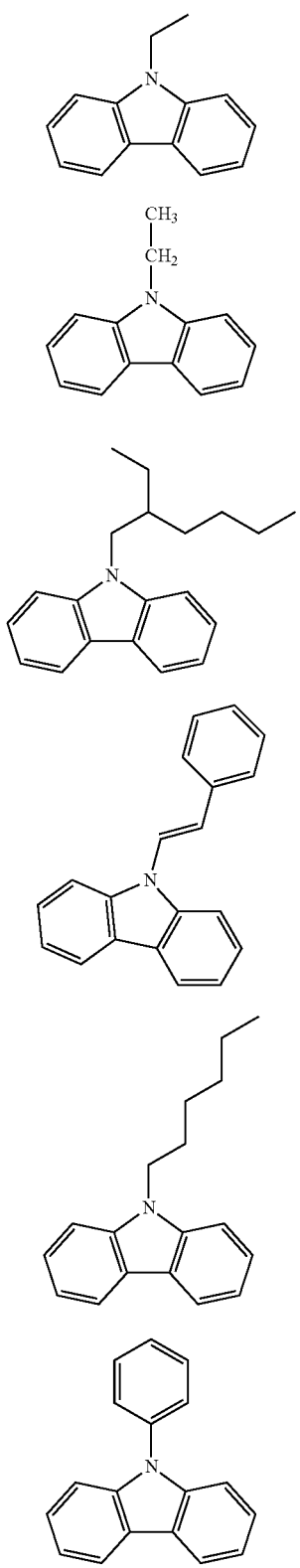

[chemical formula 4]

[chemical formula 5]

[chemical formula 6]

[chemical formula 7]

[chemical formula 8]

[chemical formula 9]

According to one embodiment of the carrier transport material, wherein the chemical structure of the polycyclic aromatic hydrocarbons (PAHs) can also be represented by following chemical formula 10 or chemical formula 11:

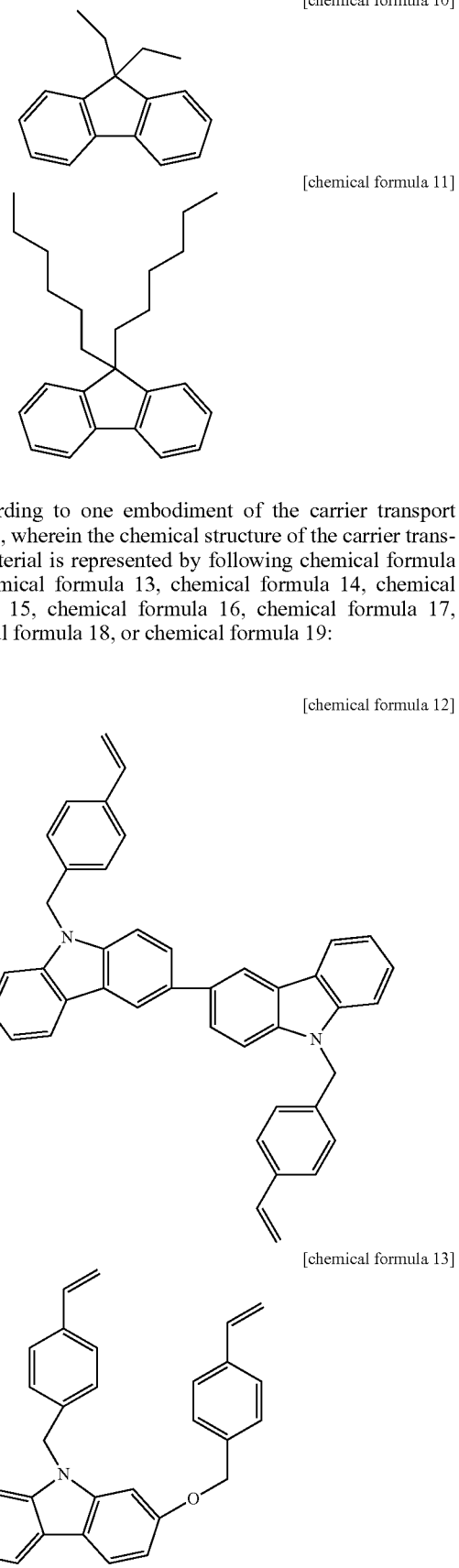

[chemical formula 10]

[chemical formula 11]

According to one embodiment of the carrier transport material, wherein the chemical structure of the carrier transport material is represented by following chemical formula 12, chemical formula 13, chemical formula 14, chemical formula 15, chemical formula 16, chemical formula 17, chemical formula 18, or chemical formula 19:

[chemical formula 12]

[chemical formula 13]

-continued

[chemical formula 14]

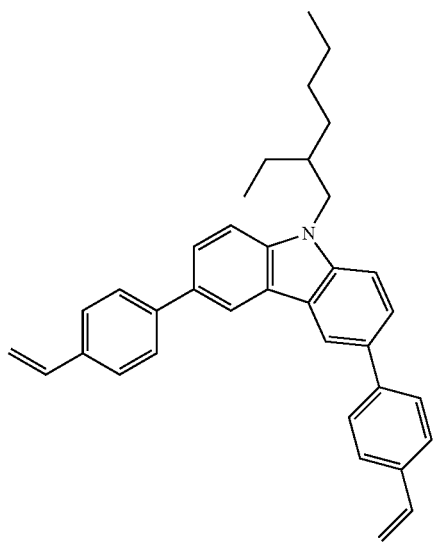

[chemical formula 15]

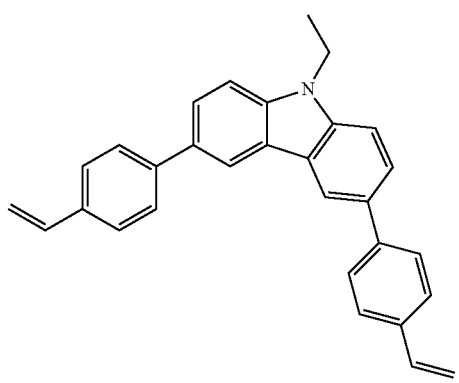

[chemical formula 16]

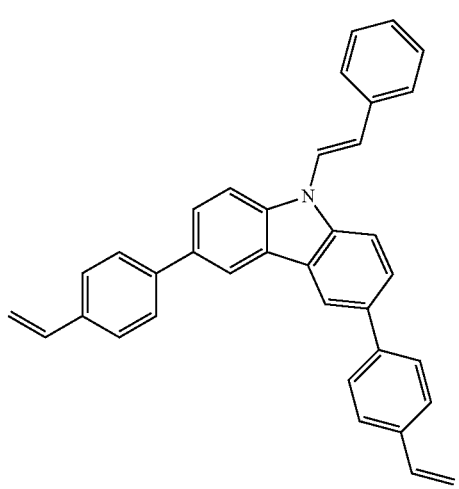

-continued

[chemical formula 17]

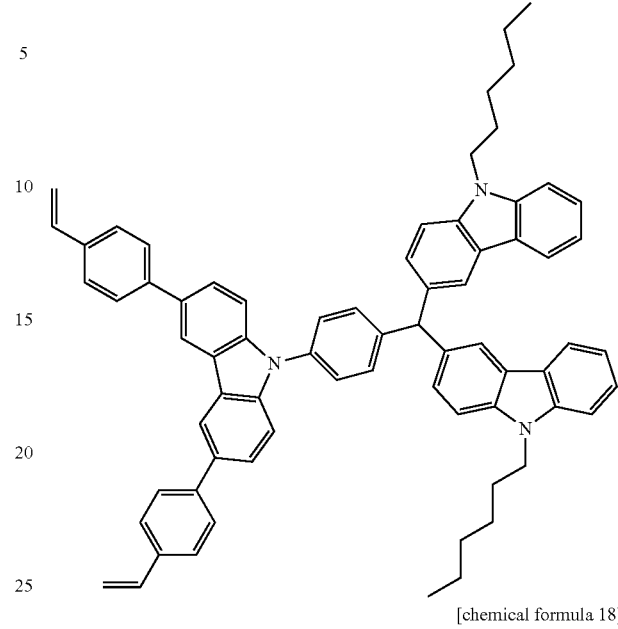

[chemical formula 18]

[chemical formula 19]

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

Figure 1:
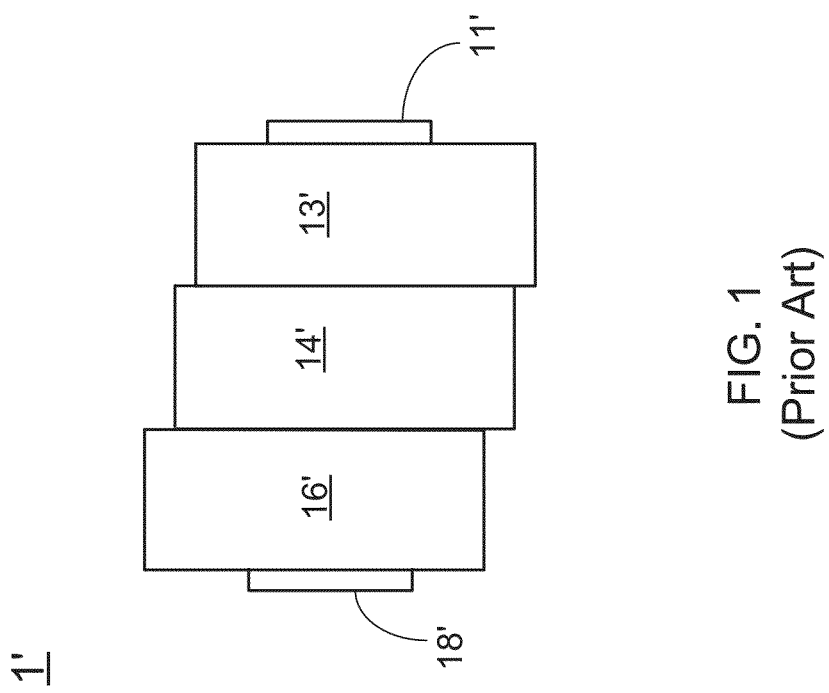
FIG. 1 is a structure diagram of a conventional organic light emitting diode (OLED)
Figure 2:
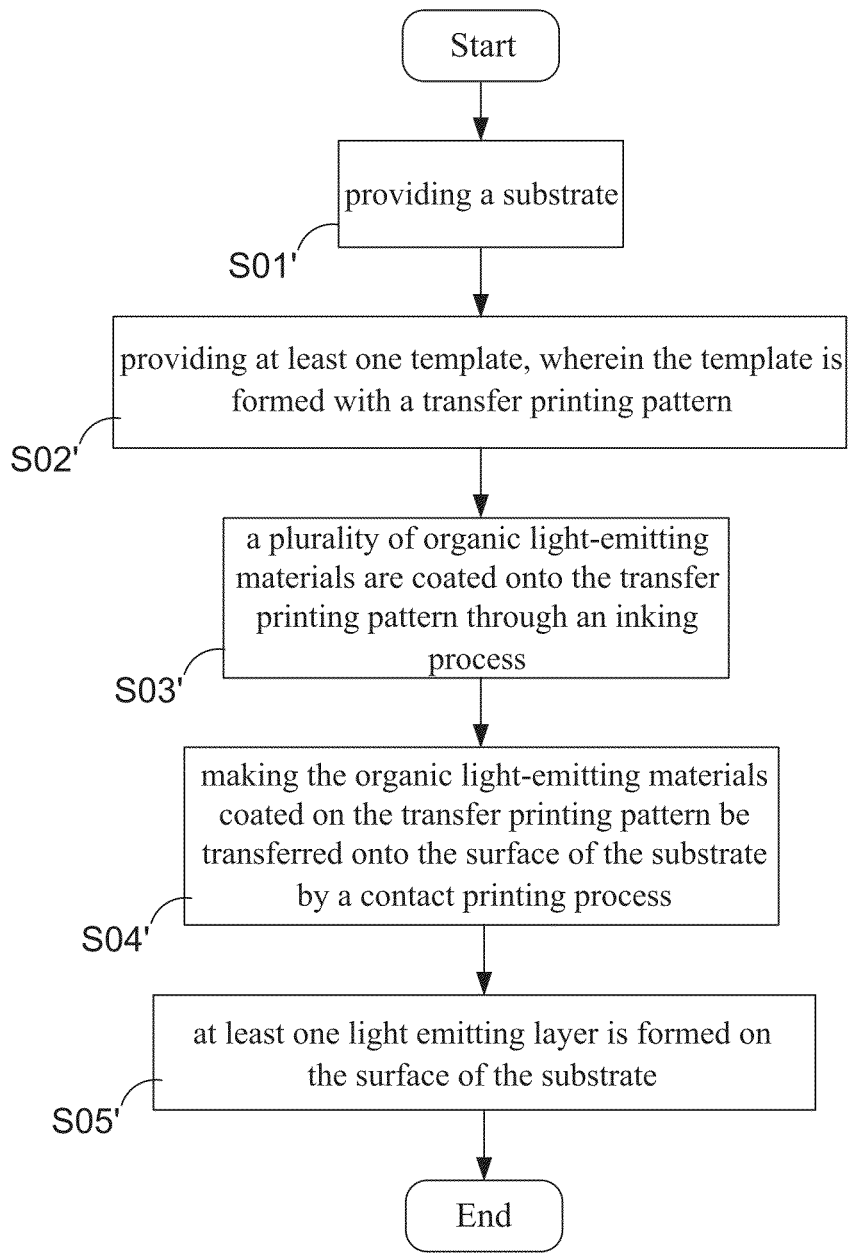
FIG. 2 is a flow chart of the solution process for manufacturing the OLED.
Figure 3:
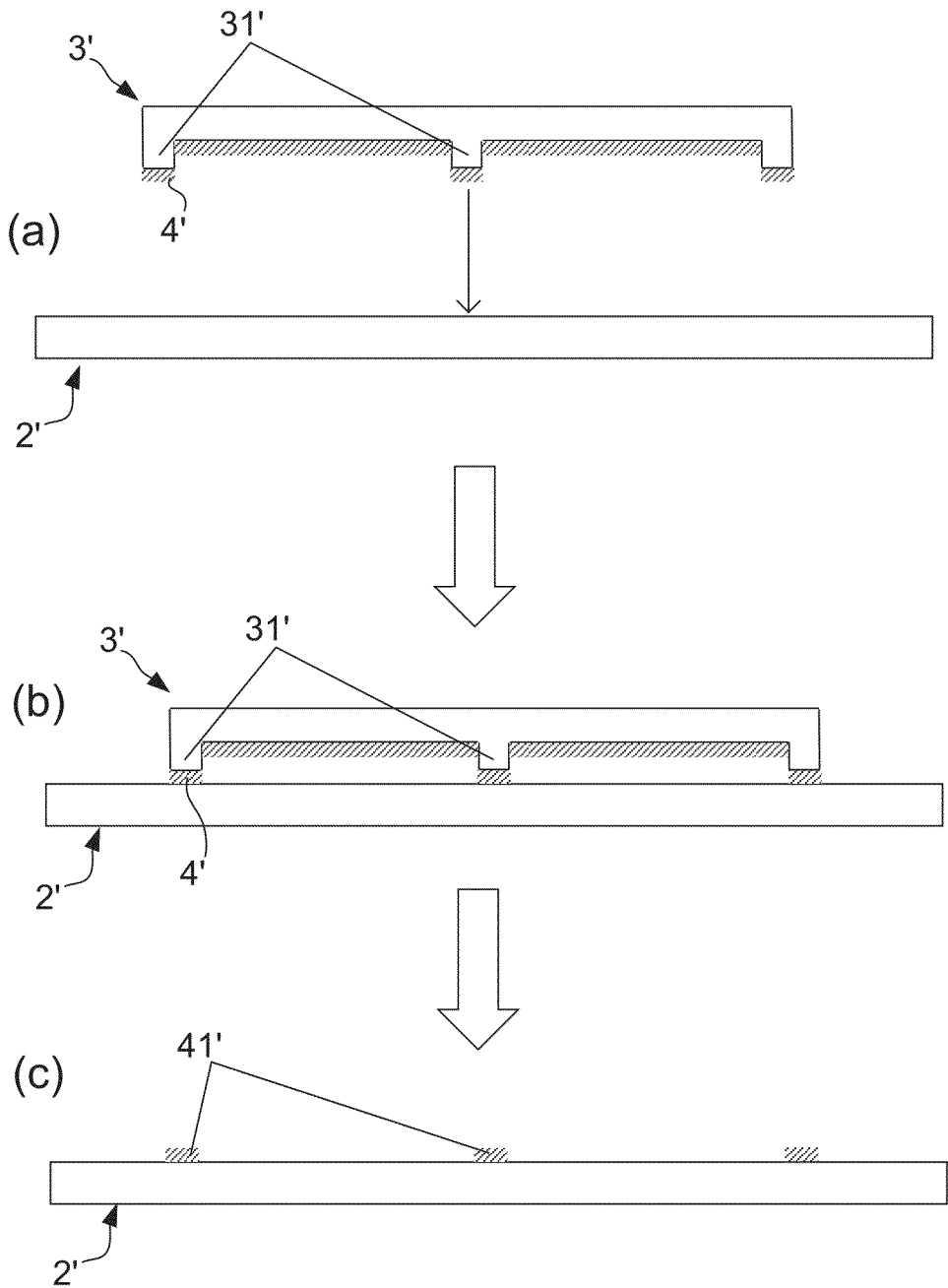
FIG. 3 shows manufacturing process diagrams of the OLED.

To more clearly describe a carrier transport material according to the present invention, embodiments of the present invention will be described in detail with reference to the attached drawings hereinafter.

The present invention provides a carrier transport material, which is formed by completing a reaction process of at least one aromatic compound and at least one polycyclic aromatic hydrocarbons (PAHs); moreover, the molecular compound has at least one cross-linkable functional group, such that a cross linking reaction can be activated in the molecular compound through heating or ultraviolet irradiation. Therefore, when the carrier transport material is applied in an OLED, the carrier transport material would not be dissolved by the solvent included in the next coated material because the carrier transport material has been cured after the cross linking reaction is carried out. Moreover, because the carrier transport material would simultaneously perform an electron confining functionality when being used as a hole transport layer, the device efficiency of the OLED having the carrier transport material is obviously enhanced during the high-brightness operation. In addition, this carrier transport material can also be applied in a solar cell.

In the present invention, the chemical structure of the aromatic compound is represented by following chemical formula 1, chemical formula 2 or chemical formula 3:

[chemical formula 1]

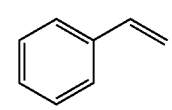

[chemical formula 2]

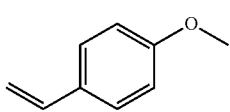

[chemical formula 3]

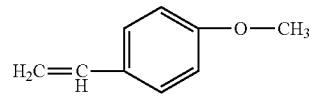

From the chemical formulas, it is able to know that the chemical formula 1 represents the chemical structure of styrene, and the chemical formulas 2 and 3 represent the chemical structure of 4-methoxystyrene. Opposite to the aromatic compound, the chemical structure of the polycyclic aromatic hydrocarbons (PAHs) is represented by following chemical formula 4, chemical formula 5, chemical formula 6, chemical formula 7, chemical formula 8, or chemical formula 9:

[chemical formula 4]

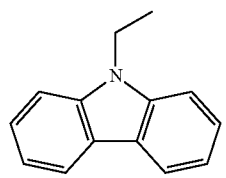

[chemical formula 5]

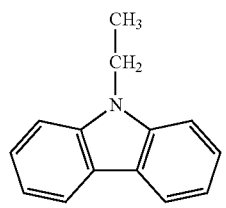

[chemical formula 6]

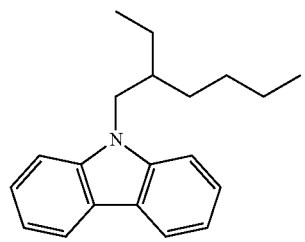

[chemical formula 7]

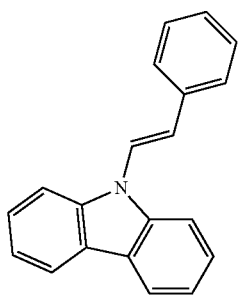

-continued

[chemical formula 8]

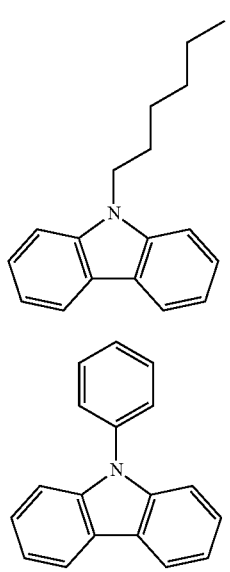

[chemical formula 9]

From the chemical formulas, it is able to know that the chemical formulas 4 and 5 represent the chemical structure of 9-ethylcarbazole, the chemical formula 6 represents the chemical structure of 9-(2-ethylhexyl)carbazole, the chemical formula 7 represents the chemical structure of 9-(2-phenylvinyl)carbazole, the chemical formula 8 represents the chemical structure of 9-hexylcarbazole, and the chemical formula 9 represents the chemical structure of 9-phenylcarbazole.

Moreover, the chemical structure of the polycyclic aromatic hydrocarbons (PAHs) can also be represented by following chemical formula 10 and chemical formula 11, wherein the chemical formula 10 represents the chemical structure of 9,9-diethylfluorene, and the chemical formula 11 represents the chemical structure of 9,9-dihexylfluorene.

[chemical formula 10]

[chemical formula 11]

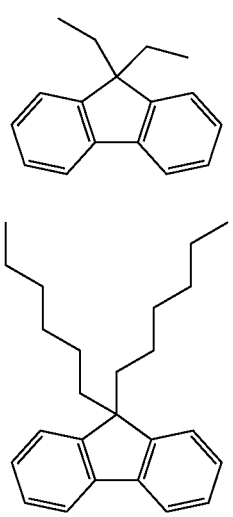

Thus, the carrier transport material of the present invention can be manufactured by completing a reaction process of the aromatic compound and the polycyclic aromatic hydrocarbons (PAHs), and the chemical structure of the carrier transport material can be represented by following chemical formula 12, chemical formula 13, chemical formula 14, chemical formula 15, chemical formula 16, chemical formula 17, chemical formula 18, or chemical formula 19:

[chemical formula 12]

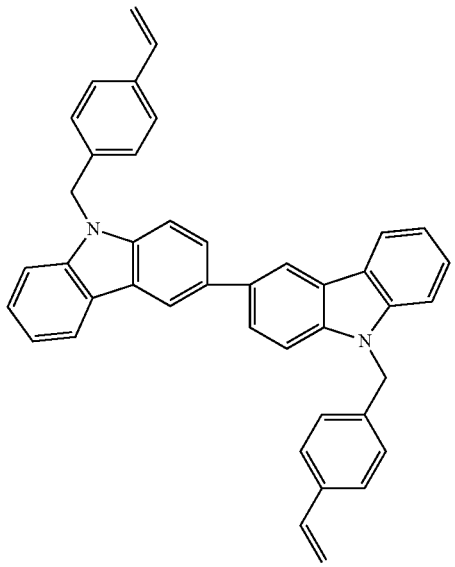

[chemical formula 13]

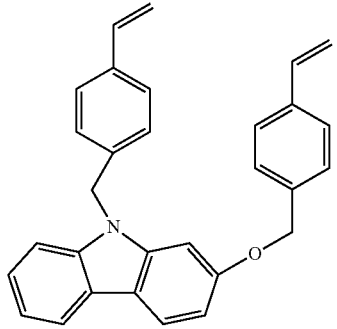

[chemical formula 14]

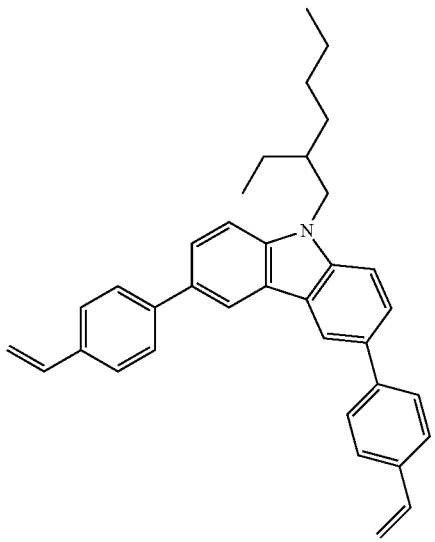

[chemical formula 15]

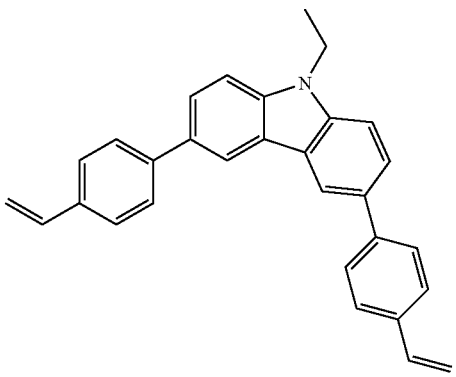

[chemical formula 16]

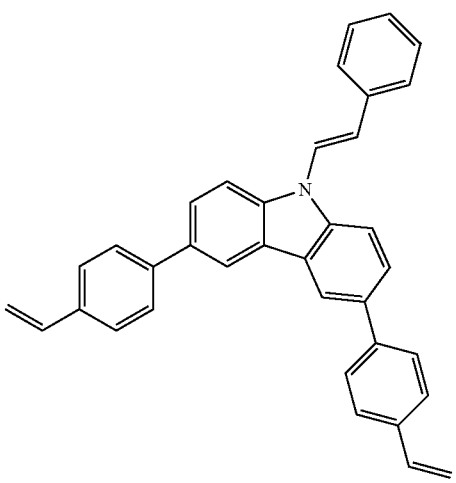

[chemical formula 17]

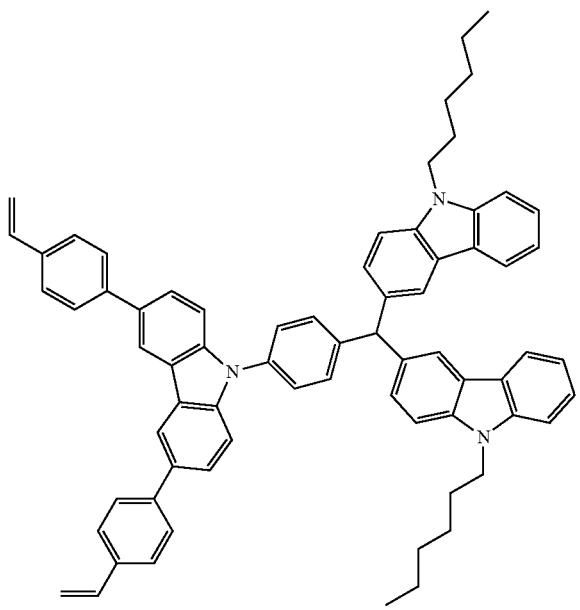

[chemical formula 18]

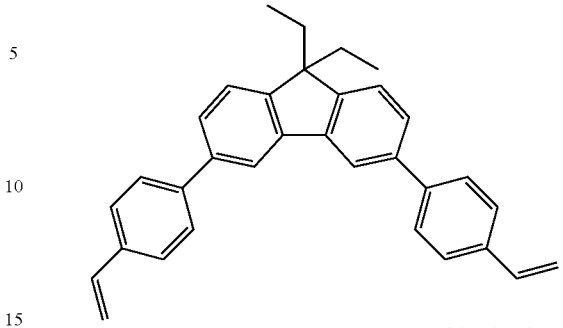

[chemical formula 19]

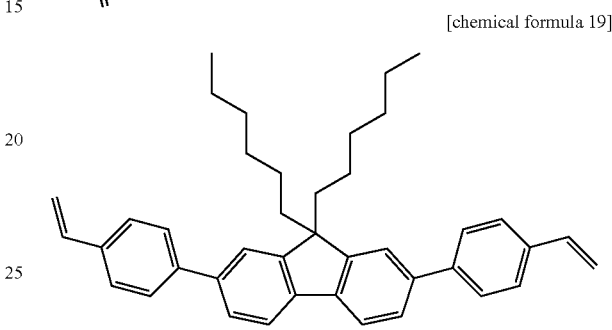

From the chemical formulas, it is able to know that the chemical formula 12 represents the chemical structure of 9,9'-Bis(4-vinyl phenyl methyl)[3,3']bicarbazole, which is called VPBC and coded with DM73 hereinafter. The chemical formula 13 represents the chemical structure of 2-(4-vinyl phenyl methoxy)-9-(4-vinyl phenyl methyl)carbazole, which is called VPOC and coded with EZK3 hereinafter.

The chemical formula 14 represents the chemical structure of 3,6-Bis(4-vinyl phenyl)-9-(2-ethylhexyl)carbazole, which is called VPEHC and coded with GK52 hereinafter. The chemical formula 15 represents the chemical structure of 3,6-Bis(4-vinyl phenyl)-9-ethylcarbazole, which is called VPEC and coded with GK60 hereinafter.

The chemical formula 16 represents the chemical structure of 3,6-Bis(4-vinyl phenyl)-9-(2-phenylvinyl)carbazole, which is called VPPC and coded with RG34 hereinafter. The chemical formula 17 represents the chemical structure of 3,6-Bis(4-vinyl phenyl)-9-{4-[di(9-hexyl carbazol-3-yl)methyl]phenyl}carbazole, which is called VPDCC and coded with RG47 hereinafter.

The chemical formula 18 represents the chemical structure of 2,7-Bis(4-vinylphenyl)-9,9-diethylfluorene, which is called VPEF and coded with GK54 hereinafter. The chemical formula 19 represents the chemical structure of 2,7-Bis(4-vinyl phenyl)-9,9-dihexyl fluorene, which is called VPHF and coded with GK101 hereinafter.

Moreover, it needs to further explain that, the carrier transport material formed by the aromatic compound and the polycyclic aromatic hydrocarbons (PAHs) has a high occupied molecular orbital energy level ($E_{HOMO}$) ranged from 5.2 eV to 6.0 eV and a lowest unoccupied molecular orbital energy level ($E_{LUMO}$) ranged from 1.8 eV to 3.2 eV.

Figure 4:
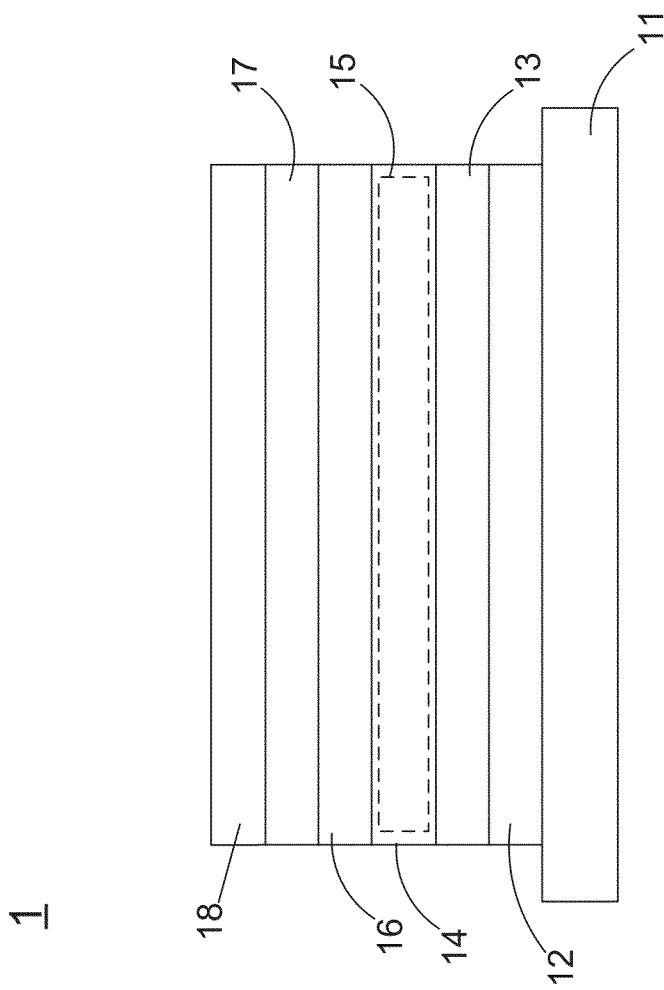
FIG. 4 is a structure diagram of an organic light emitting diode (OLED) having a carrier transport layer provided by the present invention.

Next, in order to prove that the carrier transport material of the present invention indeed can be used as a hole transport layer and/or an electron confining layer, some experiments have been finished and a verity of experiment data will be presented in following paragraphs. Please refer to FIG. 4, which illustrate structure diagram of an organic light emitting diode (OLED) having a carrier transport layer provided by the present invention. As shown in FIG. 4, the OLED 1 consists of: an anode 11, a hole injection layer 12, a hole transport layer 13, a host light emitting layer 14, a guest 15, an electron transport layer 16, an electron injection layer 17, and a cathode 18.

Figure 5:
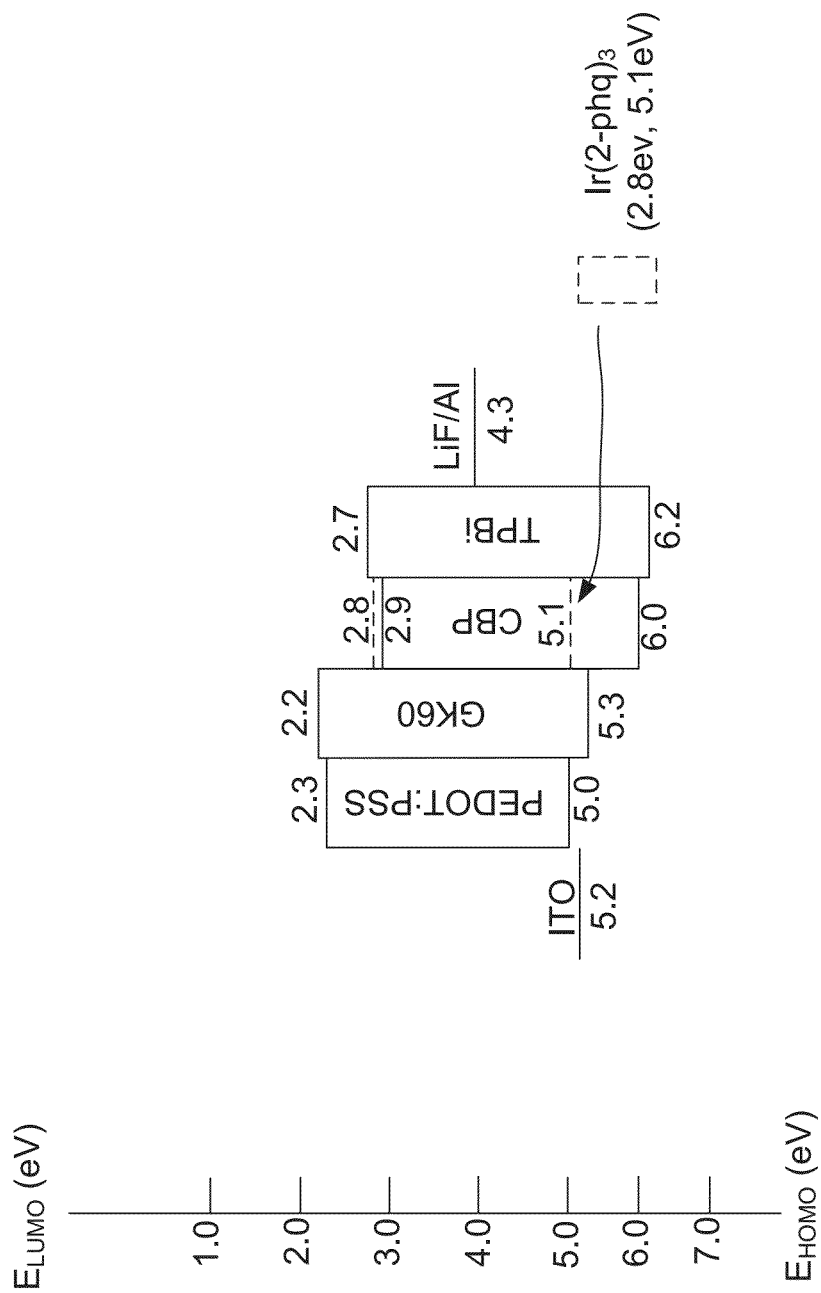
FIG. 5 shows an energy band diagram of the OLED shown by FIG. 4.

Referring to FIG. 4 again, and please simultaneously refer to FIG. 5, there is shown an energy band diagram of the OLED. As shown in FIG. 4 and FIG. 5, indium tin oxide (ITO) substrate, lithium fluorine (LiF), and aluminum (Al) are respectively used for being the anode 11, the electron injection layer 17 and the cathode 18 of the OLED 1.

Moreover, in the OLED 1, the hole injection layer 12 is made of poly(3,4-ethylene-dioxythiophene):poly-(styrenesulfonate) (i.e., PEDOT:PSS), and the electron transport layer 16 is formed by using 1,3,5-tris(N-phenylbenzimidazol-2-yl)benzene (i.e., TPBi) as the manufacturing material. Moreover, 4,4'-Bis(9H-carbazol-9-yl)biphenyl is used for being the host light emitting layer 14, and the guest dye 15 is an orange red dye of Ir(2-phq)$_3$. Furthermore, the carrier transport layer, called VPEC and coded with GK60, is used as the hole transport layer 13 of the OLED 1.

Figure 6:
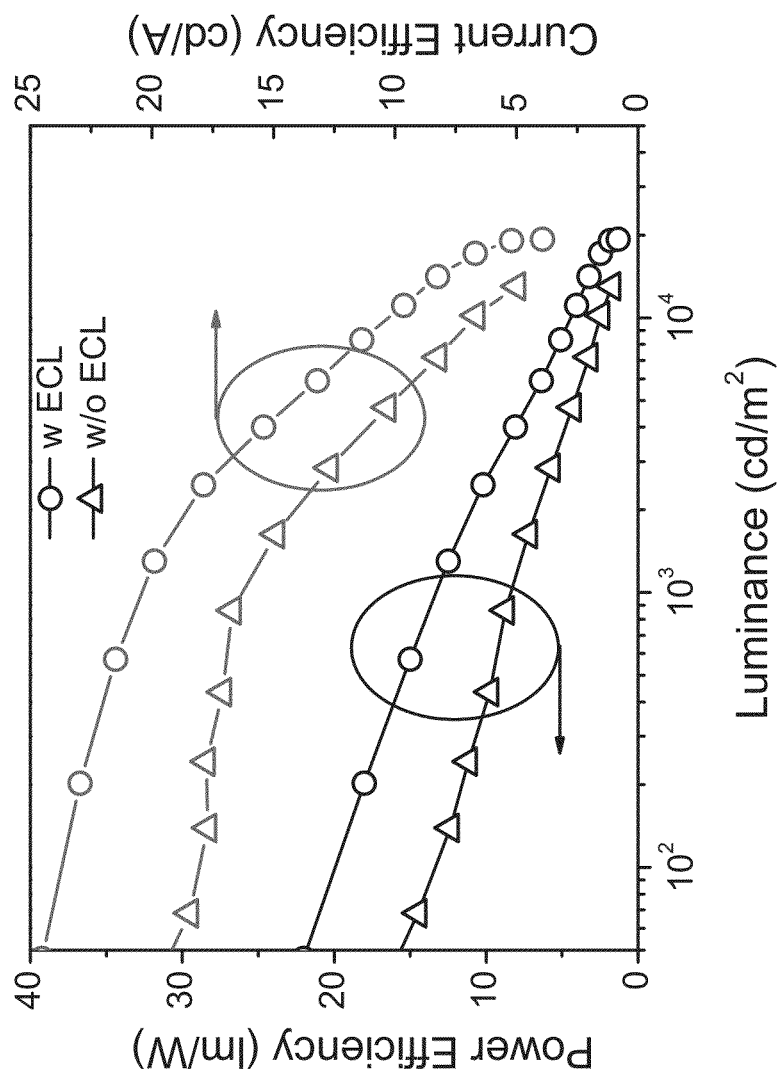
FIG. 6 shows a data plot of power efficiency versus luminance and a data plot of current efficiency versus luminance.
Figure 7:
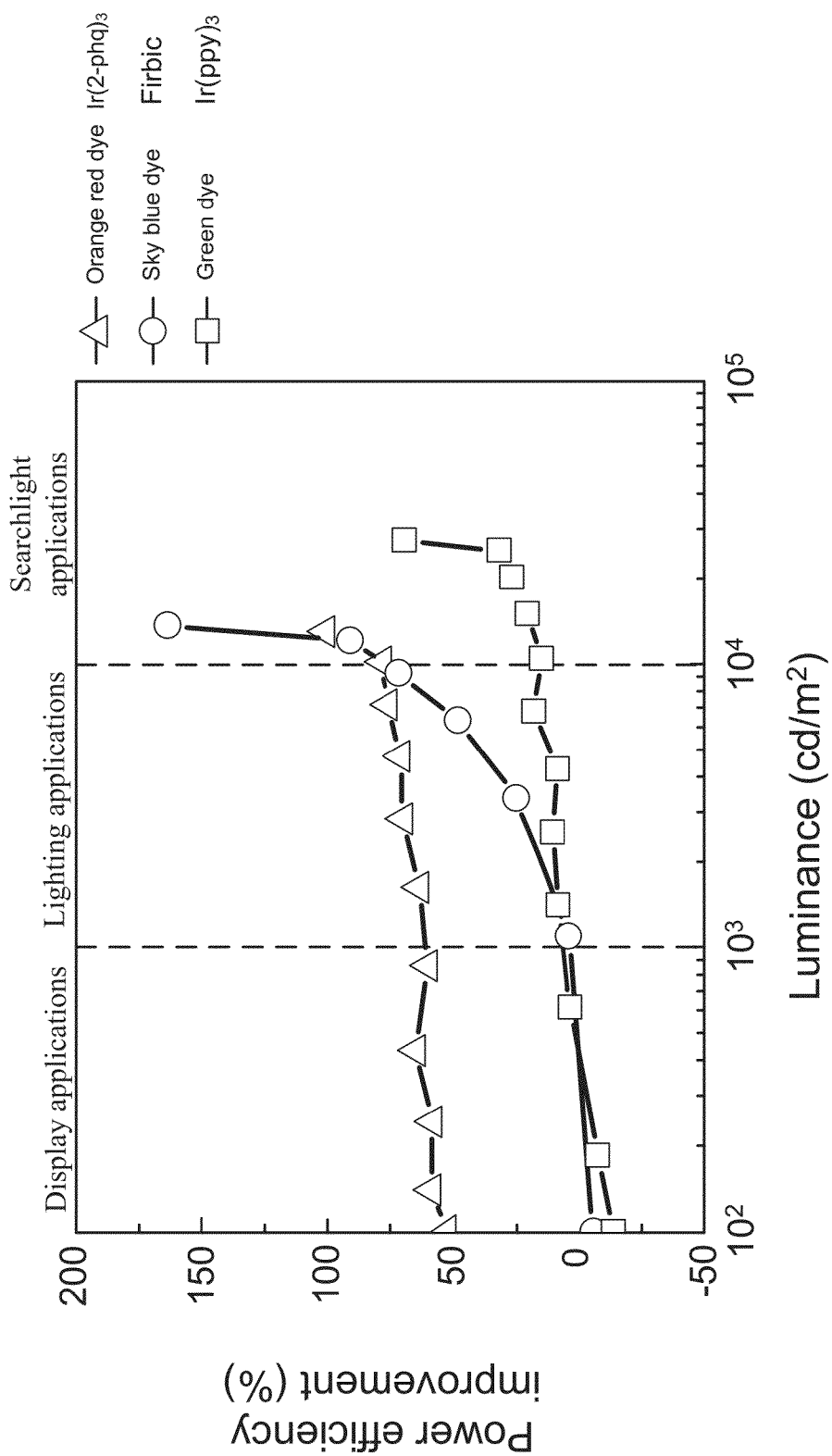
FIG. 7 shows a data plot of power efficiency improvement rate versus luminance.

FIG. 6 shows a data plot of power efficiency versus luminance and a data plot of current efficiency versus luminance. From FIG. 6, it can easily find that the OLED having the carrier transport material (i.e., GK60) provide by the present invention preforms better power efficiency and current efficiency comparing to the OLED without being provided with the carrier transport material (i.e., GK60). Furthermore, from the data plot of power efficiency improvement rate versus luminance shown in FIG. 7, it can easily know that the OLED 1 having the structure shown by FIG. 4 and the energy bane diagram shown by FIG. 5 can be applied in display filed, lighting filed and searchlight filed; Moreover, the most important is that the orange red light emitted by the OLED 1 preforms at least 50% power efficiency improvement rate.

Figure 8:
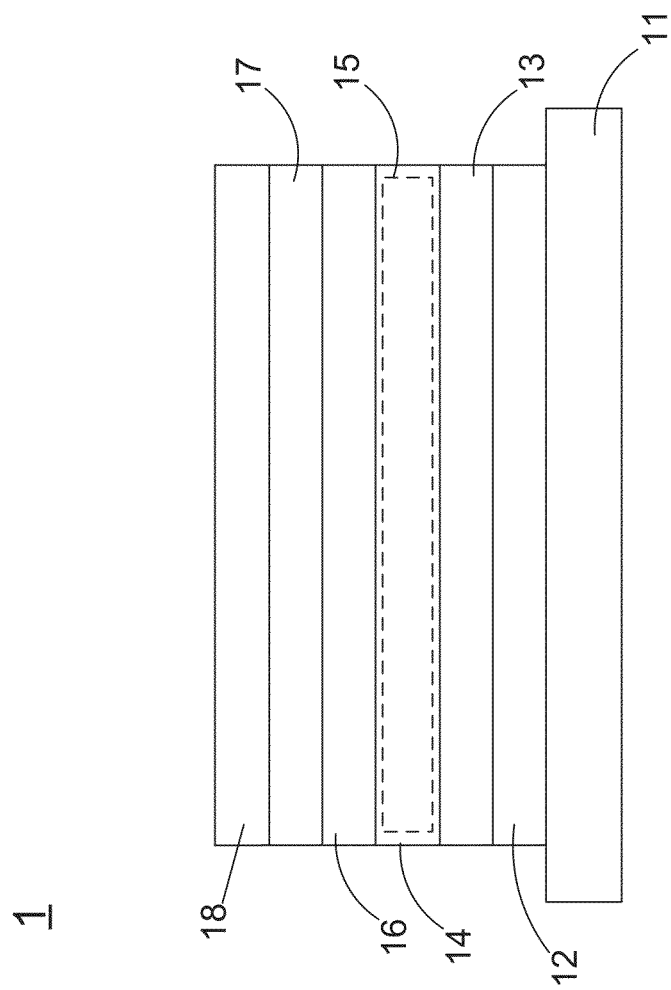
FIG. 8 is a structure diagram of an organic light emitting diode (OLED) having a carrier transport layer provided by the present invention.
Figure 9:
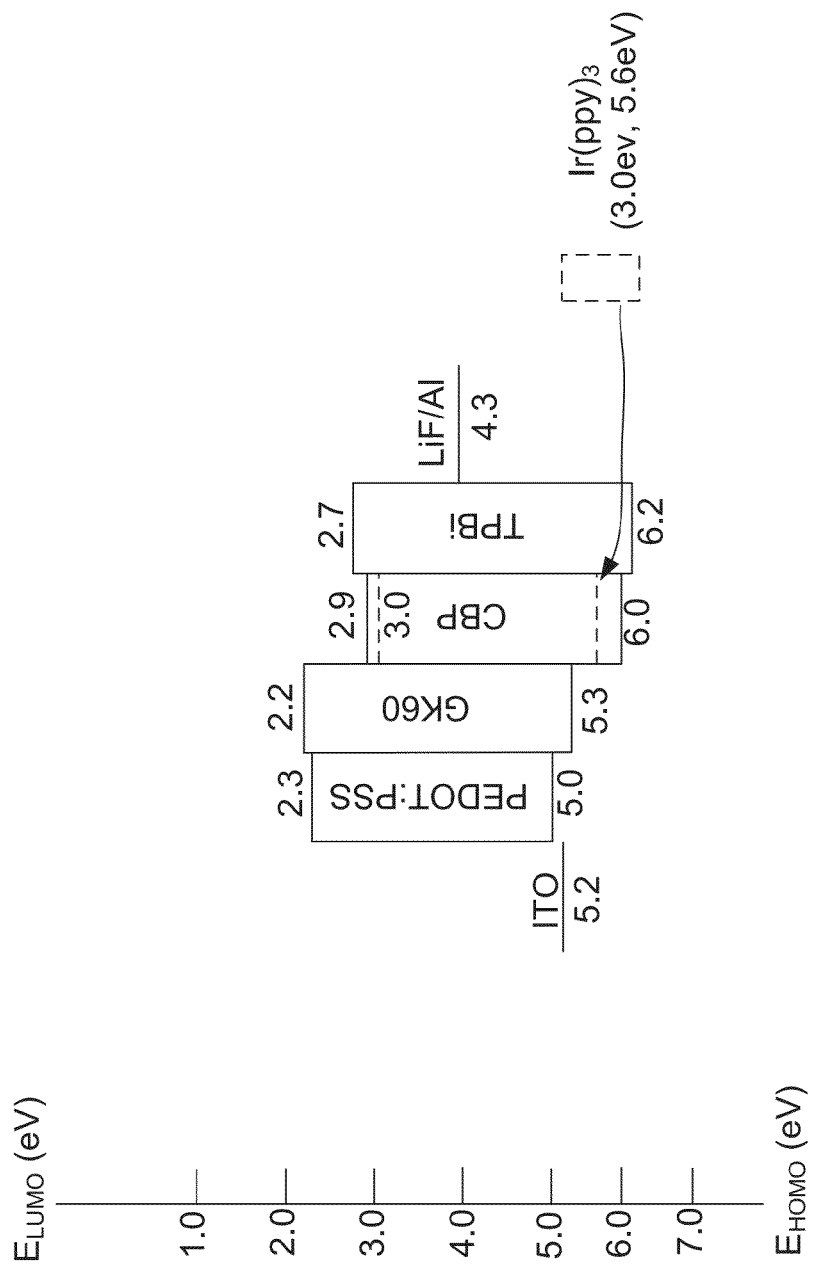
FIG. 9 shows an energy band diagram of the OLED shown by FIG. 8.

Continuously referring to FIG. 8, which illustrate a structure diagram of an organic light emitting diode (OLED) having a carrier transport layer provided by the present invention. Moreover, please simultaneously refer to FIG. 9, there is shown an energy band diagram of the OLED shown by FIG. 8. As shown in FIG. 8 and FIG. 9, the hole injection layer 12 is made of poly(3,4-ethylene-dioxythiophene):poly-(styrenesulfonate) (i.e., PEDOT:PSS), and the electron transport layer 16 is formed by using 1,3,5-tris(N-phenylbenzimidazol-2-yl)benzene (i.e., TPBi) as the manufacturing material. Moreover, 4,4'-Bis(9H-carbazol-9-yl)biphenyl (i.e., CBP) is used for being the host light emitting layer 14, and the guest dye 15 is a GREEN dye of Ir(ppy)$_3$. Furthermore, the carrier transport layer, called VPEC and coded with GK60, is used as the hole transport layer 13 of the OLED 1.

Figure 10:
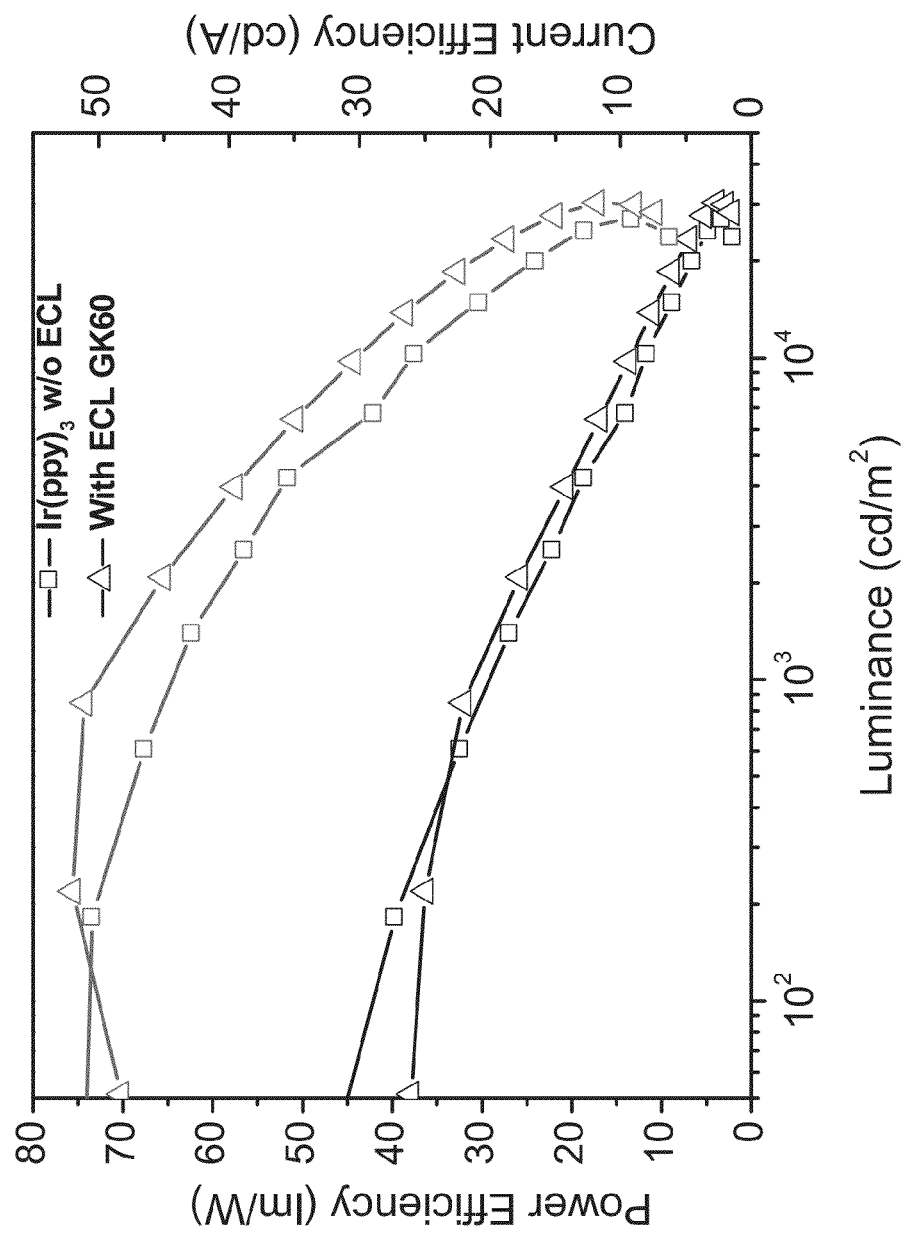
FIG. 10 shows a data plot of power efficiency improvement rate versus luminance.

FIG. 10 shows a data plot of power efficiency versus luminance and a data plot of current efficiency versus luminance. From FIG. 10, it can easily find that the OLED having the carrier transport material (i.e., GK60) provide by the present invention preforms better power efficiency and current efficiency comparing to the OLED without being provided with the carrier transport material (i.e., GK60). Furthermore, from the data plot of power efficiency improvement rate versus luminance shown in FIG. 7, it can easily know that the OLED 1 having the structure shown by FIG. 8 and the energy bane diagram shown by FIG. 9 can be applied in display filed, lighting filed and searchlight filed; Moreover, the most important is that the green light emitted by the OLED 1 preforms at least 5% power efficiency improvement rate.

Figure 11:
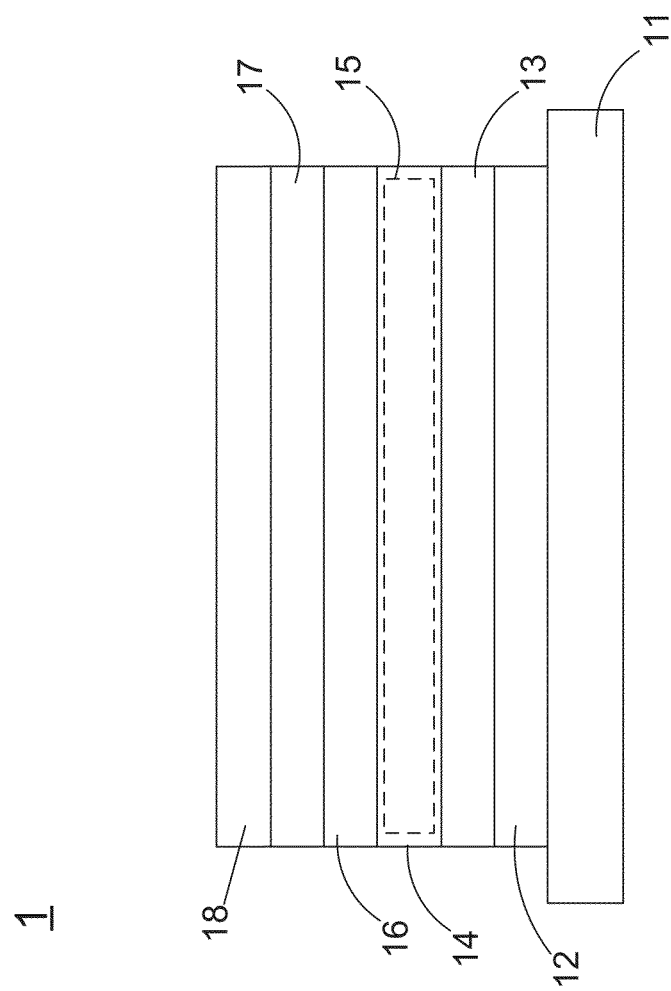
FIG. 11 is a structure diagram of an organic light emitting diode (OLED) having a carrier transport layer provided by the present invention.
Figure 12:
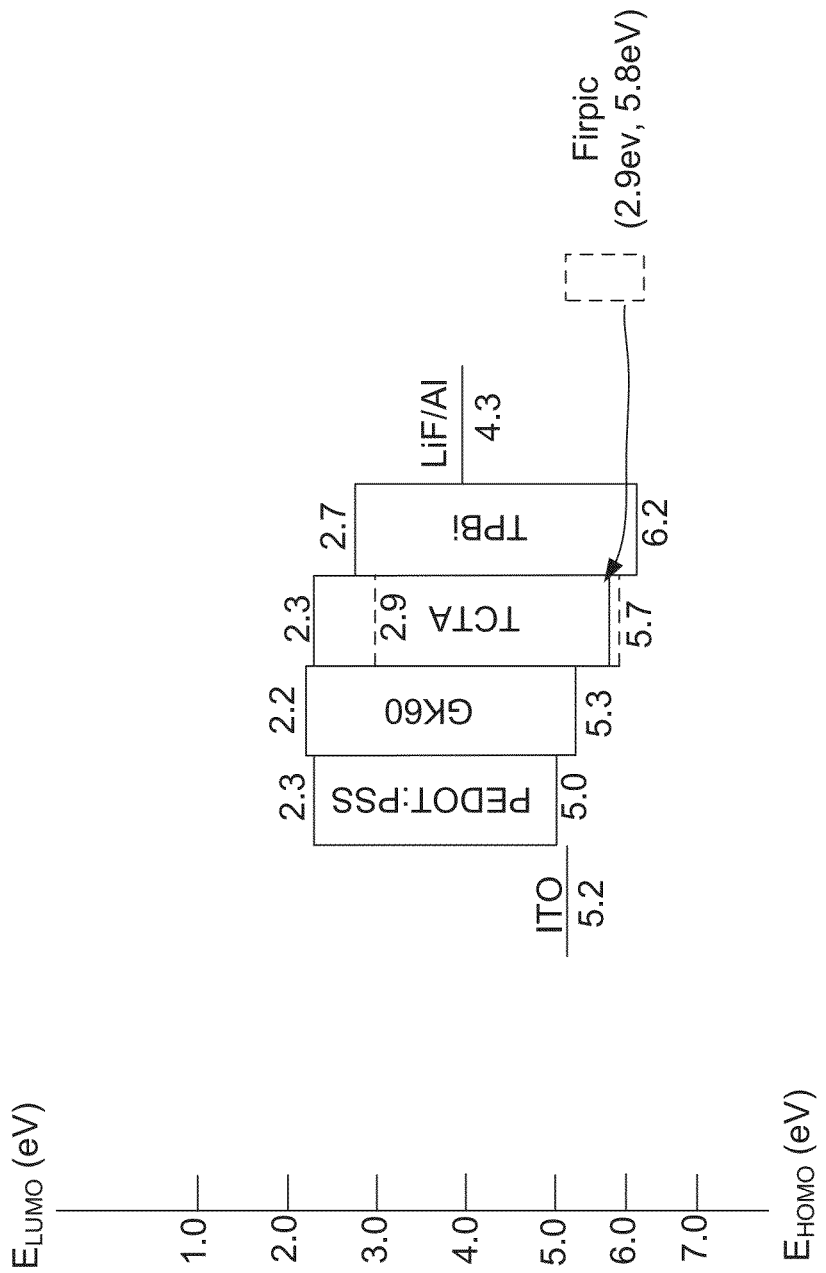
FIG. 12 shows an energy band diagram of the OLED shown by FIG. 11.

Continuously referring to FIG. 11, which illustrate a structure diagram of an organic light emitting diode (OLED) having a carrier transport layer provided by the present invention. Moreover, please simultaneously refer to FIG. 12, there is shown an energy band diagram of the OLED shown by FIG. 11. As shown in FIG. 11 and FIG. 12, the hole injection layer 12 is made of poly(3,4-ethylene-dioxythiophene):poly-(styrenesulfonate) (i.e., PEDOT:PSS), and the electron transport layer 16 is formed by using 1,3,5-tris(N-phenylbenzimidazol-2-yl)benzene (i.e., TPBi) as the manufacturing material. Moreover, 4,4',4"-Tri(9-carbazoyl)triphenylamine (i.e., TCTA) is used for being the host light emitting layer 14, and the guest dye 15 is an sky blue dye of Firpic. Furthermore, the carrier transport layer, called VPEC and coded with GK60, is used as the hole transport layer 13 of the OLED 1.

Figure 13:
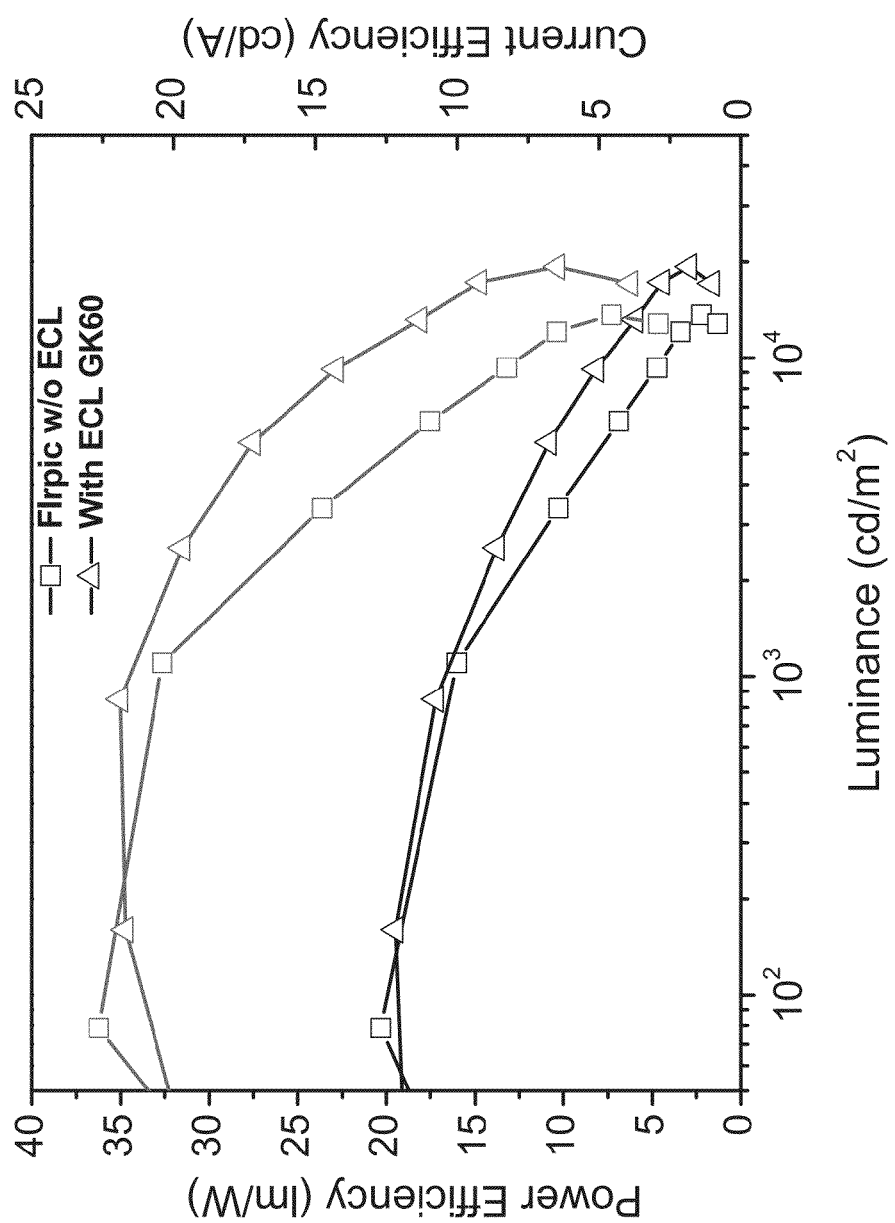
FIG. 13 shows a data plot of power efficiency improvement rate versus luminance.

FIG. 13 shows a data plot of power efficiency versus luminance and a data plot of current efficiency versus luminance. From FIG. 13, it can easily find that the OLED having the carrier transport material (i.e., GK60) provide by the present invention preforms better power efficiency and current efficiency comparing to the OLED without being provided with the carrier transport material (i.e., GK60). Furthermore, from the data plot of power efficiency improvement rate versus luminance shown in FIG. 7, it can easily know that the OLED 1 having the structure shown by FIG. 11 and the energy bane diagram shown by FIG. 12 can be applied in display filed, lighting filed and searchlight filed; Moreover, the most important is that the sky blue light emitted by the OLED 1 preforms at least 1.8% power efficiency improvement rate.

Therefore, through above descriptions, the carrier transport material proposed by the present invention has been introduced completely and clearly; in summary, the present invention includes the advantages of:

(1) carrier transport material provided by the present invention is formed by completing a reaction process of at least one aromatic compound and at least one polycyclic aromatic hydrocarbons (PAHs), wherein a cross linking reaction can be activated in the molecular compound through heating or ultraviolet irradiation because the molecular compound has at least one cross-linkable functional group. Therefore, when the carrier transport material is applied in an OLED, the carrier transport material would not be dissolved by the solvent included in the next coated material because the carrier transport material has been cured after the cross linking reaction is carried out.

(2) Moreover, because the carrier transport material would simultaneously perform an electron confining functionality when being used as a hole transport layer, the device efficiency of the OLED having the carrier transport material is obviously enhanced during the high-brightness operation.

The above description is made on embodiments of the present invention. However, the embodiments are not intended to limit scope of the present invention, and all equivalent implementations or alterations within the spirit of the present invention still fall within the scope of the present invention.

What is claimed is:

1. A carrier transport material, wherein the carrier transport material is a molecular compound formed by completing a reaction process of at least one aromatic compound and at least one polycyclic aromatic hydrocarbons (PAHs); moreover, the molecular compound having at least one cross-linkable functional group, such that a cross linking reaction can be activated in the molecular compound through heating or ultraviolet irradiation;

wherein the chemical structure of the carrier transport material is represented by following chemical formula 13, chemical formula 14, chemical formula 15, chemical formula 16, or chemical formula 17:

[chemical formula 13]
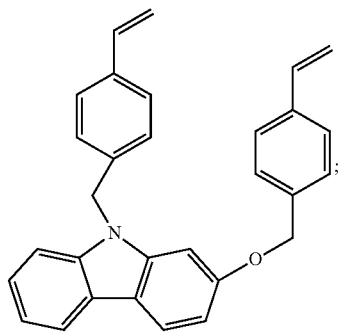
[chemical formula 14]
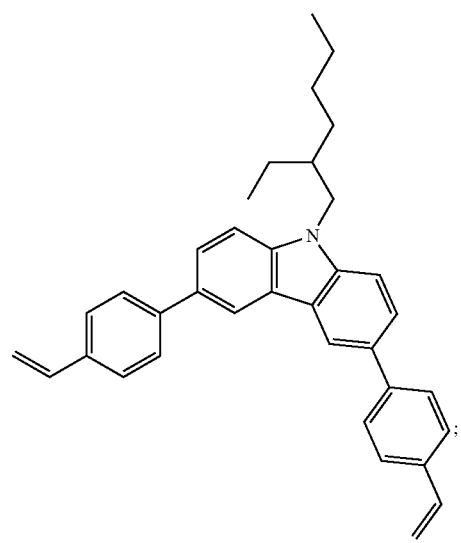
[chemical formula 15]
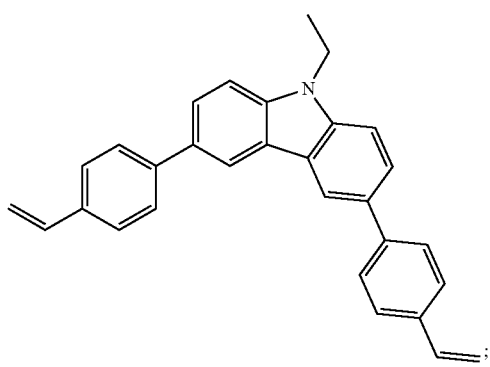
[chemical formula 16]
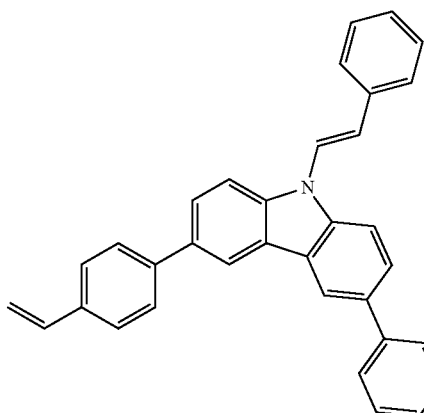
[chemical formula 17]
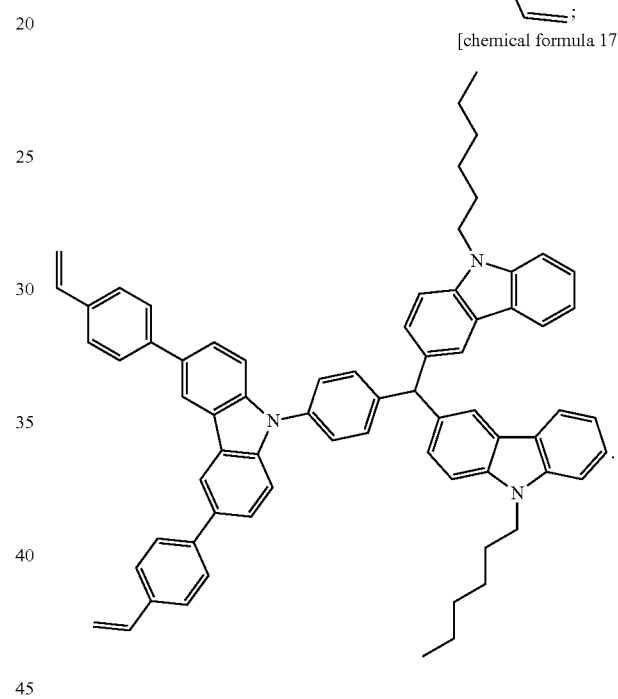
2. The carrier transport material of claim 1, wherein the carrier transport material has a high occupied molecular orbital energy level (EHOMO) ranged from 5.2 eV to 6.0 eV and a lowest unoccupied molecular orbital energy level (ELUMO) ranged from 1.8 eV to 3.2 eV.
* * * * *